(12) United States Patent
Pronovost et al.

(10) Patent No.: US 6,656,744 B2
(45) Date of Patent: Dec. 2, 2003

(54) ONE-STEP LATERAL FLOW ASSAYS

(75) Inventors: Allan D. Pronovost, San Diego, CA (US); Hans Boehringer, San Diego, CA (US); Ya-Chen Hsu, Sunnyvale, CA (US)

(73) Assignee: Quidel Corporation, San Diego, CA (US)

( * ) Notice: Subject to any disclaimer, the term of this patent is extended or adjusted under 35 U.S.C. 154(b) by 0 days.

(21) Appl. No.: 09/510,595

(22) Filed: Feb. 22, 2000

(65) Prior Publication Data

US 2002/0146844 A1 Oct. 10, 2002

Related U.S. Application Data

(63) Continuation of application No. 08/700,663, filed on Aug. 9, 1996, now abandoned.
(60) Provisional application No. 60/002,777, filed on Aug. 9, 1995.

(51) Int. Cl.[7] ............................................. G01N 33/558
(52) U.S. Cl. .................... 436/514; 436/65; 436/536; 436/518; 436/814; 422/55; 422/56; 422/57; 422/58; 422/61; 422/65; 435/7.1; 435/4; 435/5; 435/7.9; 435/7.92; 435/7.93; 435/7.94; 435/975; 435/805
(58) Field of Search .................. 435/4, 5, 7.1, 7.9, 435/7.92, 7.93–7.94, 975, 805; 422/55, 56, 57, 58, 61, 65; 436/65, 514, 536, 814, 518

(56) References Cited

U.S. PATENT DOCUMENTS

| | | | |
|---|---|---|---|
| 4,298,685 A | 11/1981 | Parikh et al. ................... 435/7 |
| 4,366,241 A | 12/1982 | Tom et al. ...................... 435/7 |
| 4,496,654 A | 1/1985 | Katz et al. ..................... 435/7 |
| 4,737,453 A | 4/1988 | Primus .......................... 435/5 |
| 4,806,311 A | 2/1989 | Greenquist ................... 422/56 |
| 4,861,711 A | 8/1989 | Friesen et al. ................. 436/7 |

(List continued on next page.)

FOREIGN PATENT DOCUMENTS

| | | |
|---|---|---|
| WO | WO 88/08534 | 11/1988 |
| WO | WO 92/02428 | 2/1992 |
| WO | WO 93/03175 | 2/1993 |
| WO | 93/03175 | * 2/1993 |
| WO | WO 94/01775 | 1/1994 |

OTHER PUBLICATIONS

Wilchek, M et al, Anal. Biochem. vol 171(1), pp. 1–32, 1988.*
Blake et al., "Use of Enzymes in Immunoassay Techniques A Review," *Analyst* (1984) 109(5):533–547.
Diamandis et al., "The Biotin–(Strept) Avidin System: Principles and Applications in Biotechnology," *Clin Chem* (1991) 37(5):625–636.
Diamandis, "Analytical Methodology for immunoassays and DNA Hybridization Assays—Current Status and Selected Systems—Critical Review," *Clinica Chimica Acta* (1990) 194(1):19–50.
Ishikawa et al., "Ultrasensitive Enzyme Immunoassays, "*Clinica Chimica Acta* (1990) 194(1):51–72.
Wilchek et al., "The Avidin–Biotin Complex in Bioanayltical Applications," *Anal Biochem* (1988) 171(1):1–32.

*Primary Examiner*—Lynette R. F. Smith
*Assistant Examiner*—Ginny Allen Portner
(74) *Attorney, Agent, or Firm*—Morrison & Foerster LLP

(57) ABSTRACT

The efficiency and accuracy of one-step lateral flow assays can be improved by employing more efficient binding between participants in labeling and capture. Thus, in addition to analyte/anti-analyte interactions, specific binding is achieved through members of an irrelevant specific binding pair. Also included within the invention is a format wherein unlabeled competitor for analyte serves as a gatekeeper in the capture zone, competing with analyte for labeled anti-analyte, which analyte will be captured in a detecting portion of a capture zone.

6 Claims, 5 Drawing Sheets

Before Analyte

After Analyte

U.S. PATENT DOCUMENTS

Figure 1:
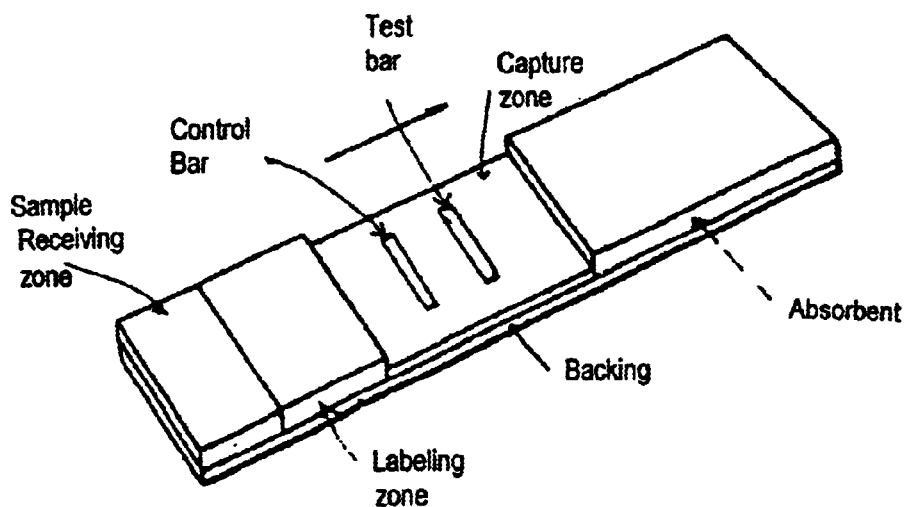

| | | | | |
|---|---|---|---|---|
| 4,870,007 A | * | 9/1989 | Smith-Lewis | 435/28 |
| 4,891,313 A | | 1/1990 | Berger et al. | 436/7 |
| 4,943,522 A | | 7/1990 | Eisinger et al. | 435/7 |
| 5,001,049 A | | 3/1991 | Klein et al. | 435/5 |
| 5,030,558 A | * | 7/1991 | Litman et al. | 435/7.91 |
| 5,047,326 A | | 9/1991 | Pronovost | 435/7.36 |
| 5,079,142 A | | 1/1992 | Coleman et al. | 435/7.92 |
| 5,081,013 A | | 1/1992 | Rovelli et al. | 435/7.92 |
| 5,089,423 A | | 2/1992 | Diamandis et al. | 436/518 |
| 5,126,241 A | | 6/1992 | Schenk | 435/7.1 |
| 5,141,850 A | | 8/1992 | Cole et al. | 436/525 |
| 5,164,294 A | | 11/1992 | Skold et al. | 435/7.5 |
| 5,200,317 A | | 4/1993 | Georgevich | 435/7.4 |
| 5,212,063 A | | 5/1993 | Ofenloch-Hahnle et al. | 435/7.5 |
| RE34,312 E | | 7/1993 | Geiger et al. | 435/5 |
| 5,232,835 A | | 8/1993 | Litman et al. | 435/7.93 |
| 5,260,194 A | | 11/1993 | Olson | 435/7.91 |
| 5,310,650 A | | 5/1994 | McMahon et al. | 435/6 |
| 5,354,692 A | | 10/1994 | Yang et al. | 436/514 |
| 5,384,264 A | | 1/1995 | Chen et al. | 436/525 |
| 5,415,994 A | | 5/1995 | Imrich et al. | 435/5 |
| 5,424,193 A | | 6/1995 | Pronovost et al. | 435/7.32 |
| 5,424,220 A | | 6/1995 | Goerlach-Graw | 436/568 |
| 5,432,057 A | | 7/1995 | Litman et al. | 435/7.91 |
| 5,500,375 A | | 3/1996 | Lee-Own et al. | 436/514 |
| 5,521,102 A | | 5/1996 | Boehringer et al. | 435/523 |
| 5,527,711 A | * | 6/1996 | Tom-Moy et al. | 436/518 |
| 5,534,620 A | | 7/1996 | Oh et al. | 530/413 |
| 5,541,069 A | | 7/1996 | Mortensen et al. | 435/7.9 |
| 5,622,871 A | | 4/1997 | May et al. | 436/514 |
| 5,648,274 A | * | 7/1997 | Chandler | 436/514 |
| 5,674,698 A | * | 10/1997 | Zarling et al. | 435/7.92 |
| 5,686,315 A | | 11/1997 | Pronovost et al. | 436/510 |
| 5,716,778 A | | 2/1998 | Weng et al. | 435/4 |
| 5,741,662 A | * | 4/1998 | Madsen et al. | 435/34 |
| 5,766,961 A | * | 6/1998 | Pawlak et al. | 436/510 |
| 5,770,460 A | * | 6/1998 | Pawlak et al. | 436/510 |
| 5,798,273 A | * | 8/1998 | Shuler et al. | 436/514 |
| 5,945,294 A | * | 8/1999 | Frank et al. | 435/7.9 |
| 6,037,127 A | * | 3/2000 | Ebersole et al. | 435/6 |
| 6,319,676 B1 | * | 11/2001 | Nazareth et al. | 435/7.5 |
| 6,399,397 B1 | * | 6/2002 | Zarling et al. | 436/518 |

\* cited by examiner

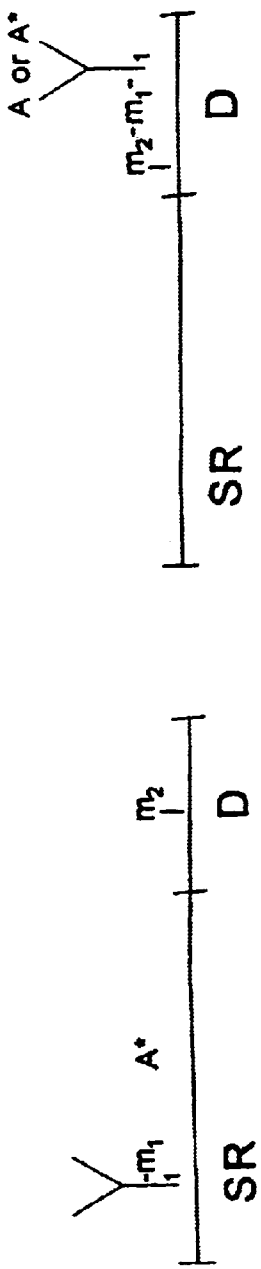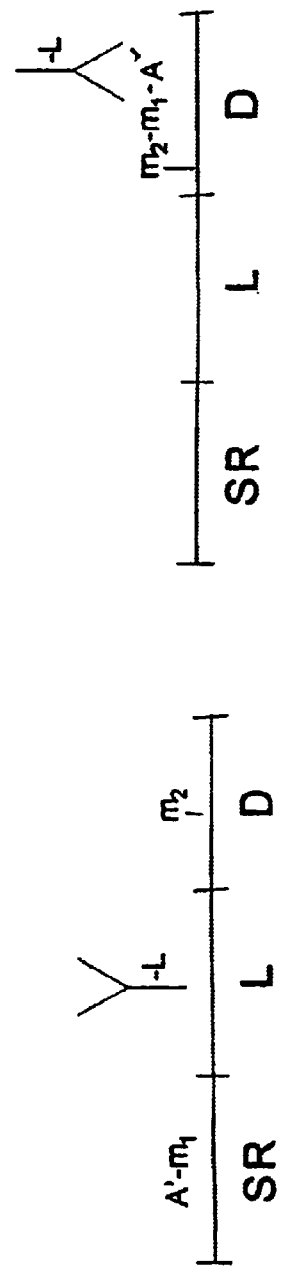

ONE-STEP LATERAL FLOW ASSAYS

This application is a continuation of U.S. patent application Ser. No. 08/700,663, filed Aug. 9, 1996, now abandoned, which claims priority benefit of Provisional U.S. Patent Application Ser. No. 60/002,777, filed Aug. 9, 1995 under 35 U.S.C. §119(e) now abandoned.

TECHNICAL FIELD

The invention is in the field of immunoassays. More specifically, it relates to one-step lateral flow assays wherein an analyte is applied to a test strip in a sample zone and detected in a capture zone. The invention provides means for improving the speed and accuracy of such assays.

BACKGROUND ART

One-step nonbibulous lateral flow assays are described in WO92/12428 published Jul. 23, 1992. In the exemplified version of these assays, a sample containing analyte is applied to a sample zone in a nonbibulous matrix which permits nonchromatographic flow of solution components. The analyte travels through the labeling zone containing antibody to analyte coupled with visible label. The analyte picks up labeled antibody and the sample flows, thence, to a capture zone where the complex of analyte and labeled anti-analyte is captured and detected in a sandwich using an additional anti-analyte component adsorbed in the capture zone on a "test bar". A control bar in the capture zone contains biotinylated rabbit γ-globulin which captures label coupled to avidin. This control label travels along with the sample into the capture zone. The background section of WO92/12428 describes and cites additional patent publications relating to other format' for lateral flow assays.

In addition, PCT Application WO94/01775 published Jan. 20, 1994 describes similar one-step lateral flow assay procedures and devices wherein the anti-analyte in the labeling zone is coupled to a visible label in a particular way. Antibody to analyte is coupled to an enzyme that converts a substrate to a colored-dye, which dye then complexes with the enzyme/anti-analyte to provide a visible label. Again, the analyte is detected in a capture zone as a sandwich using a different antibody specifically reactive with analyte on the test bar.

The efficiency and accuracy of the self-contained, lateral flow, double-antibody sandwich immunoassays described in these PCT Applications depends not only on the ability of the label to be released readily from the labeling zone with sufficient rapidity upon contact with the sample, but also on the speed of binding of labeled anti-analyte to any analyte contained in the sample and of binding of analyte to the anti-analyte contained in the capture zone.

The general principle of such assays has also been applied to antibody detection where at least one anti-analyte may be an antigen. In this case, the sandwich contains a specific antiglobulin for the antibody to be detected, and a labeled form of the antigen for this antibody. Competitive formats for these assays have also been devised. In all of these formats, the rate of interaction of the components is significant.

The interaction of labeled anti-analyte and analyte must take place within 30 seconds or less and capture must occur rapidly as well. In the event that the labeled anti-analyte interaction with analyte and the capture of the resulting complex in the capture zone do not occur within the required times, which is often the case, a more efficient system for labeling and capture needs to be used. The present invention provides such efficient labeling and capture systems by supplementing the anti-analyte/analyte interactions with other, more efficient, specific binding pair interactions, such as the interaction of biotin and avidin or streptavidin.

Biotin/streptavidin interactions have been utilized in other ways in immunoassay procedures for some time. For example, in U.S. Pat. No. 5,126,241, streptavidin adsorbed to solid support is used to bind biotinylated antigen in a procedure which involves incubation to form a complex in which the analyte to be determined competes with label and solid support for access to an antibody capable of binding all three. U.S. Pat. No. 4,496,654 describes an assay for human chorionic gonadotropin conducted by binding biotinylated antibody to an avidin-coupled paper disk, reacting the antibody on a disk with a solution suspected of containing hCG, and then determining the amount of hCG on the disk using standard determination techniques. This assay results in a sandwich of hCG formed from anti-hCG bound to solid support through biotin/avidin linkage and labeled anti-hCG. This assay does not involve a lateral flow of sample.

U.S. Pat. No. 5,001,049 describes a method for determining antibodies against human HIV which involves incubating streptavidin-derivatized solid support with a biotinylated peptide reactive with anti-HIV, and then detecting any bound antibody with labeled antibody receptor. Again, lateral flow does not take place in these assays. RE 34,132, which is a reissue of U.S. Pat. No. 4,945,042, describes a direct assay for an antibody wherein the antibody to be determined serves as a link between a labeled epitope and an epitope bound to substrate through a streptavidin/biotin link. Again, speed of reaction is not critical, since a lateral flow format is not required.

Disclosure of the Invention

The invention provides means to improve the efficiency of one-step lateral flow assays by expediting labeling and/or capture reactions that result in the detection of analyte, and by a novel strategy for the design of competition protocols. In general, in some of these assays, the analyte is detected as a labeled sandwich containing the analyte captured in a detection zone. In the improved methods of the invention as applied to these assays, a member of a specific binding pair with a specificity irrelevant to analyte/anti-analyte interaction is coupled the label, to a mobile anti-analyte, to the "capture" anti-analyte in the nondetecting portion of the capture zone, or to a competitor to the analyte in the sample-receiving zone and is used to effect binding of label to analyte-containing complex or of complex to solid support.

Thus, in one aspect, the invention is directed to a method to determine the presence, absence or amount of an analyte in a sample in a one-step lateral flow assay conducted on a test strip. The test strip has a sample-receiving zone, an optional labeling zone, and a capture zone. The method comprises applying the sample to the sample-receiving zone, allowing the sample to proceed through the labeling zone, if present, to the capture zone and assessing the capture zone for the presence, absence or amount of label in the capture zone. The analyte complexed or coupled to the label, or a labeled competitor of the analyte, is typically captured in a detection bar in the capture zone.

In a direct assay, the analyte is captured as a sandwich comprising two anti-analytes, one of said anti-analytes is bound to the detection bar and the other anti-analyte is bound or coupled to a label. At least one of said label and the solid matrix in said detection bar is bound to an anti-analyte through members of a specific binding pair irrelevant to the specificity of the analyte/anti-analyte interaction.

In one competitive format, labeled competitor is added to the sample before the sample is applied to the sample-receiving zone, or is itself contained in the sample-receiving zone where labeled competitor competes for anti-analyte coupled to a member of the irrelevant specific binding pair, and the resulting complexes are carried to the detection zone where labeled competitor is detected; the amount of the labeled competitor in the detection zone is inversely proportional to the amount of analyte in the sample. In this format, of course, no labeling zone may be necessary.

In additional improvements included within the scope of the invention, unlabeled competitor is used in the assay. In one approach, the competitor for analyte is coupled to a member of a specific binding pair irrelevant to the analyte/anti-analyte interaction, which member permits the competitor to be captured in the detection zone by its counterpart. The competitor bearing the specific binding pair member is typically supplied in the sample-receiving zone or is mixed with the sample prior to application to the sample-receiving zone. The coupled competitor and the analyte then compete for labeled anti-analyte in the labeling zone; only the competitor (bearing the labeled anti-analyte) is captured in the detection zone; analyte bound to label is lost. Thus, again, the amount of label detected is inversely proportional to the concentration of analyte.

In still another embodiment of the competitive format, unlabeled analyte or analogous competitor behaves as a gatekeeper to prevent analyte carrying label into the detection zone. The competitor is contained in a portion of the capture zone proximal to the sample receiving zone. Binding in the detection zone may be either through anti-analyte adsorbed thereto, or through a member of a specific binding pair with specificity irrelevant to the analyte/anti-analyte interaction as described above.

In additional aspects, the invention is related to test strips for the performance of the method of the invention. Such test strips contain a sample-receiving zone, an optional labeling zone, and a capture zone, wherein at least one of said zones contains a substance that includes one member of a nonanalyte-related specific binding pair, and another zone contains the counterpart member of said nonanalyte related specific binding pair.

In embodiments wherein a competitor for anti-analyte behaves as a gatekeeper to the detecting portion of a capture zone, the invention is related to test strips having a sample-receiving zone, a labeling zone and a capture zone wherein the capture zone is divided into at least two portions; a gatekeeper portion and a detecting portion wherein said gatekeeping portion is located on the test strip between the labeling zone and the detecting portion, i.e., proximal to the sample-receiving zone. The labeling zone of said test strips contains a label coupled to anti-analyte, which anti-analyte is optionally coupled to one member of a specific binding pair with specificity irrelevant to analyte/anti-analyte interaction. The detecting zone contains a second anti-analyte or a counterpart binding pair member as appropriate.

In still another aspect, the invention relates to complexes which comprise analyte sandwiched between two anti-analyte components, at least one of said anti-analyte components being coupled to label or to a support matrix through counterpart members of a specific binding pair unrelated to analyte.

A BRIEF DESCRIPTION OF THE DRAWINGS

FIG. 1 shows a typical test strip useful in the method of the invention containing a sample-receiving zone, a labeling zone, and a capture/detection zone.

FIGS. 2A–2H are diagrammatic representations of specific embodiments of the invention. SR: sample receiving zone; L: labeling zone; D: capture zone; $D^1$: gatekeeping zone; $D^2$: detecting zone; A: analyte; Y: anti-analyte; $m_1$: first member of a specific binding pair with specificity irrelevant to analyte/anti-analyte interaction; $m_2$: second member (or counter member) of a specific binding pair with specificity irrelevant to analyte/anti-analyte interaction; $m_3$: first member of a second specific binding pair with specificity irrelevant to analyte/anti-analyte interaction; $m_4$: second member (or counter member) of a second specific binding pair with specificity irrelevant to analyte/anti-analyte interaction; L: label; A*: labeled competitor for the analyte; and A': competitor for the analyte.

Figure 3:
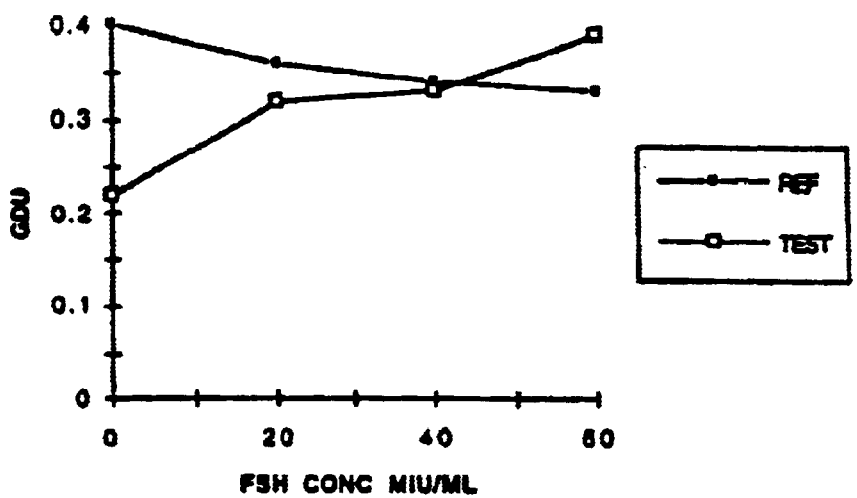

FIG. 3 is a graphical representation of the results of an assay according to the method of invention for FSH.

MODES OF CARRYING OUT THE INVENTION

The assays for which the methods and materials of the invention are almost useful are those which depend on speed of interaction as the sample travels through a test strip, which strip can be described as a "support matrix", "solid support", and the like. In general, these are lateral flow devices, where a sample containing an analyte is permitted to traverse the test strip and is detected by capture of a detectable moiety in a specified detection zone.

Many devices of this type have been described. A particularly useful device is described in WO92/12428, the contents of which are incorporated herein by reference. Briefly, the device contains a sample-receiving zone, a labeling zone, and a capture zone (or detection zone). The zones are constructed separately and placed into liquid communication; the capture or detection zone is abutted to an absorbent which enhances the flow of sample through the strip. The strip is prepared in separate sections so that the conditions for associating the appropriate moiety with the solid matrix support can be regulated. The label in the labeling zone must be capable of being mobilized to flow with the sample when attached to analyte; the capturing agent must remain in the detection zone.

Thus, in a typical construction, the sample-receiving zone will be constructed from a support matrix that is normally nonbibulous, such as the inert support marketed as Porex™ or will be constructed of a substrate with moderate bibulous nature such as spun nylon, which will then be pre-treated with a blocking agent to confer nonbibulous characteristics. Suitable blocking agents include, for example, methylated BSA. The labeling zone also must permit free flow of sample and mobilization of the label when the sample flows through. Therefore, the labeling zone will be pre-blocked, if necessary, and lyophilized, if necessary, to permit the label to flow freely. Similar treatment will be accorded the sample-receiving zone if it contains, as it does in the embodiments preferred herein, a reagent which must be mobilized after binding to analyte. The capture zone will generally be a support which is capable of strong adsorptive capacity so that the capturing agent is not liberated from the capture zone when the sample traverses it. Thus, in general, the capture reagent is first adsorbed to the capture zone and subsequent to the adsorption, blocking is provided to assure smooth liquid flow.

In typical embodiments, the capturing agent for the analyte will be included only in a portion of the capture zone, i.e., for example, a "test bar" or "detection bar" which will be visible or otherwise detectable when analyte is present.

The test bar can be of any desired shape; a simple line is often convenient, although for aesthetic reasons, sometimes a plus sign (+) is used. Limiting the capturing agent for the analyte to only a portion of the capture zone permits space to provide a control wherein, in another portion of the capture zone a "control bar" is constructed containing a capturing agent that is irrelevant to the analyte but designed to capture label traversing the capture zone from the labeling zone. For example, the control bar might include an antibody to a ligand different from analyte which ligand is coupled to label and mixed with label intended for analyte in the labeling zone.

In certain embodiments of the invention, it is mandatory for the capture zone to be divided into at least two portions. This is the case, in particular, where a competitive form of the analyte serves as a "gatekeeper" in a portion of the detecting zone. In these embodiments, label will generally appear in both sections of the detecting zone, and it is mandatory clearly to distinguish between that containing the gatekeeper (symbolized in the figures as $D^1$) and that containing the test compound ($D^2$). Of course, these formats can also be designed to contain a "control bar" as described above, but it should not be necessary in this case since the portion occupied by the gatekeeper can reasonably serve that function.

If, according to the method of the invention, a specific binding pair comprising small molecules such as biotin/streptavidin is used as a capture mechanism, the biotin or preferably the streptavidin, will be adsorbed to the test bar or control bar after complexing the streptavidin with irrelevant antibody or other protein to improve retention characteristics. Thus, as illustrated below, avidin or streptavidin is best retained in the capture zone when first complexed with γ-globulin or BSA. It will be noted that in the embodiment of the invention wherein a competitor to the analyte serves as a gatekeeper in a portion of the capture zone, it is not always necessary to employ the specific binding pair with specificity irrelevant to analyte/anti-analyte interaction.

Other formats and methods of construction may, of course, also be used. For example, other test strips contain support matrixes that are continuous, and the various zones are obtained by treating different regions along the strip with a different reagents. Supports which permit the relatively free flow of sample and its components are preferred—i.e., supports which do not effect chromatographic separations of sample components. However, there is no theoretical reason that the techniques of the invention could not be applied to supports which have some adsorptive capacity, such as paper. The methods and devices of the invention are suitable for test strips in general, whatever their supporting material, so long as they contain, in liquid communication, a sample-receiving zone, an optional labeling zone, and a detection zone. The labeling zone must be present when a direct detection of analyte is desired using a sandwich-type complex. A labeling zone is unnecessary when a label is added directly to the sample as a competitor for a capture agent to the analyte.

The formats of the assays can also vary. The assay may be direct, i.e., the analyte may be labeled with one specific anti-analyte component and captured by another, or it may be competitive, e.g., the analyte may compete with a labeled competitor for capture in the detecting zone. In other examples of a competitive-type assay, the competitor of the analyte need not be labeled. For instance, the competitor may still compete with analyte for label while the competitor, alone, is coupled to a member of a specific binding pair irrelevant to analyte/anti-analyte interaction wherein the counterpart member of the pair is adsorbed to the detection zone. In other embodiments, the competitor acts as a gatekeeper in a portion of the capture zone preceding the capture reagent; this competitor captures some of the label and prevents it from entering the formal detecting portion of the capture zone.

This format offers the possibility to preset a detection level for the analyte by regulating the amount of competitor (labeled A' in the drawings) in the gatekeeping portion. By elevating the level of A', a higher analyte concentration will be required to be detectable in the detecting zone. The strip could also be modified so that varying levels of A' are included in the gatekeeper zone across the bias of the strip so that the proportion of the width of the strip that gives a detectable reading in the detecting portion can be assessed as a measure of analyte concentration.

The analyte may be any substance, and may itself be an antibody or a fragment of an antibody.

In general, the specificity of the assay for a desired analyte is conferred by the presence of at least one anti-analyte component. By "anti-analyte" is meant any substance which binds comparatively more strongly to the analyte then to any other components likely to be contained in the sample. Typical anti-analytes include antibodies and immunologically reactive fragments thereof, such as $F_{ab}$, $F_{ab}'$ and $F_{(ab2)}'$ fragments, or generically-engineered fragments, such as Fv fragments. Other anti-analyte interactions are provided by receptor/ligand interactions, for example. Any substance which binds specifically to analyte to the relative exclusion of other components is classified as an "anti-analyte" herein.

In the competition format of the invention, the competitor of the analyte can either be labeled or unlabeled depending on the protocol. By "competitor of analyte" is meant any substance which competes with the analyte for binding to anti-analyte. Typically, the competitor is simply the analyte itself either modified by providing it with a label or with a member of a specific binding pair to distinguish it from analyte per se, or analyte itself positioned at the gatekeeping portion of a test strip on which the assays are conducted.

In the description below, "coupled" in generally used when covalent bonding is intended, "bound" includes non-covalent interactions, as well. The nature of the interaction, however, will generally be clear from the context.

In one format that forms the basis for the improvement of the invention, the analyte is labeled by an anti-analyte coupled to label and captured by an anti-analyte which is itself is bound to at least a portion of the capture zone. The amount of label determined in the capture zone is then directly proportional to the amount of analyte in the sample. In a different format, the analyte may compete with an already labeled competitor for the capture anti-analyte which is ultimately bound to the capture zone. In this embodiment, no labeling zone is required.

The detection of the analyte in the "test bar" (or of the control in the control bar) which are in the capture zone is achieved by methods appropriate to the label. In the most convenient and preferred formulation of the assay, a visible label is used. Visible labels include colored latex beads, various metal sols, complexed dye-conjugates, and the like. Under these circumstances, the results can be detected visually and the test is greatly simplified. However, there is no inherent reason other forms of labeling could not be used, including radioactive isotopes, florescent labels, and enzyme labels. In these cases, additional steps directed towards detection may be required, for example, to detect an enzyme label, it would be necessary to supply substrate to measure the enzyme activity. A broad range of labeling possibilities is available and known to practitioners in the art.

In the improved formats of the invention, either the binding of label to anti-analyte or binding of anti-analyte to the capture zone is effected through counterpart members of a specific binding pair irrelevant to the interaction of the analyte with anti-analyte. Typical such specific binding pairs might include biotin/avidin, biotin/streptavidin, antibody/antigen combinations other than analyte/anti-analyte and receptor/ligand combinations other than analyte/anti-analyte. Such specific combinations include rhodamine/anti-rhodamine; FITC/anti-FITC; DNP/anti-DNP; and mouse IgG/anti-mouse IgG.

The specific binding pair member can be coupled to anti-analyte or to label using standard covalent binding techniques generally known in the art. The component may be linked directly, or more typically, through spacer arms or linkers including, for example, commercially available homofunctional or heterofunctional linkers. Such methods of coupling are standard in the art and can be optimized for a particular choices, nonanalyte related specific binding pair members ($m_n$) and for particular anti-analytes. Although anti-analytes have been symbolized in FIGS. 2A–2H as antibodies, as explained above, this need not be the case. Indeed, this notation is used simply to make clear which component is the anti-analyte component without the necessity for elaborate systems of symbolism. It is again emphasized that the "Y" antibody symbol simply represents, in this context, an anti-analyte compound. This could be a receptor for a ligand which constitutes the analyte, a ligand for a receptor that constitutes the analyte, an antigen for an antibody that constitutes the analyte, and the like. Any components specifically binding to anti-analyte will suffice.

Typical arrangements are shown diagrammatically in FIGS. 2A–2H.

Figure 2A:
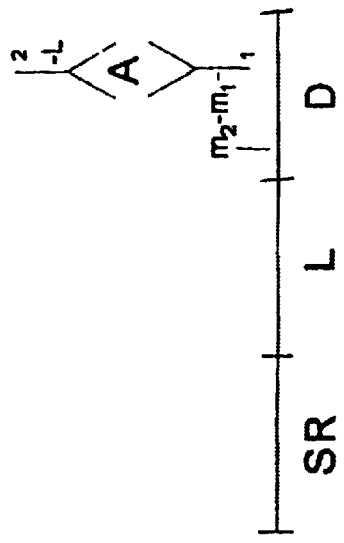
Figure 2A:
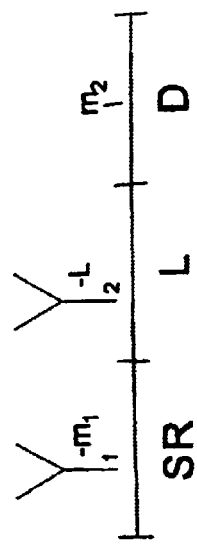

In FIG. 2A, a direct assay format is depicted. The sample-receiving zone contains a first anti-analyte coupled to a member of an alternative specific binding pair, $m_1$. The labelling zone contains a second anti-analyte coupled to the label where L denotes the detectable label; the capture zone contains the counterpart to $m_1$, which is denoted $m_2$. When analyte flows through the test strip, it picks up anti-analyte/$m_1$ from the sample-receiving zone and labeled anti-analyte from the labeling zone and travels as a sandwich complex to the capture zone, wherein $m_1$ binds $m_2$ to retain the complex. The final complex will then be: support/$m_2$/$m_1$/anti-analyte$_1$/analyte/labeled anti-analyte$_2$. In this format, the interaction of $m_1$ and $m_2$ expedites the capture of the sandwich in the detection zone.

Figure 2B:
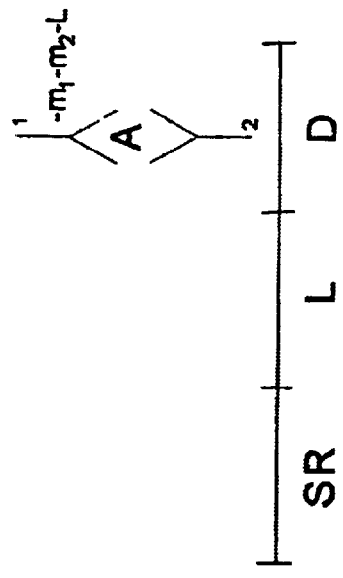
Figure 2B:
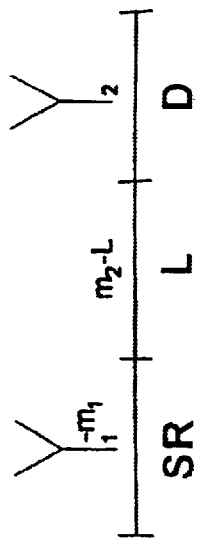

In FIG. 2B, another direct assay is depicted. The sample-receiving zone again contains a first anti-analyte coupled to $m_1$, label coupled to $m_2$ is in the labeling zone; a second anti-analyte is adsorbed to the capture zone in a "test bar". As analyte travels through the test strip, it picks up anti-analyte/$m_1$ from the sample-receiving zone; $m_1$ binds $m_2$ coupled to label in the labeling zone, and the analyte sandwich (the analyte/anti-analyte/$m_1$/$m_2$/label complex), travels to the capture zone to obtain the complex bound to support: support/anti-analyte$_2$/analyte/anti-analyte$_1$/$m_1$/$m_2$/label. In this format, the $m_1$/$m_2$ interaction assists in the interaction between label and the anti-analyte-bound analyte.

Figure 2C:
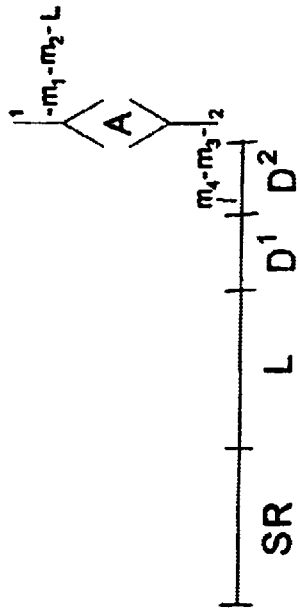
Figure 2C:
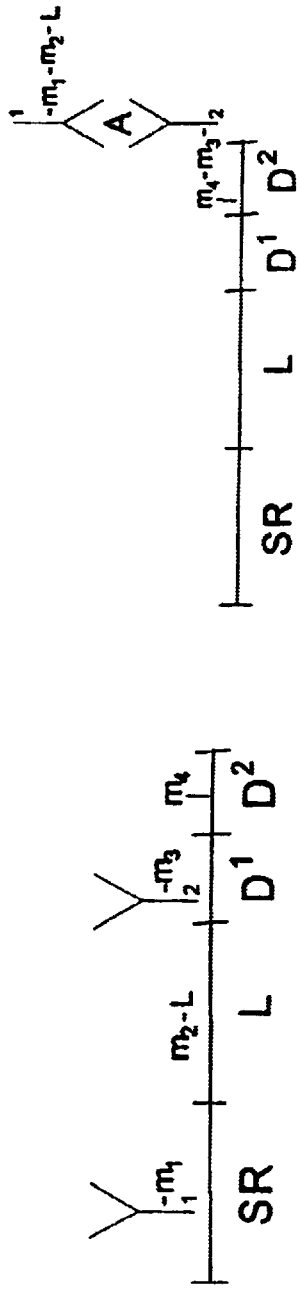

These two complementary binding methods are both utilized in the direct assay as shown in FIG. 2C wherein $m_1$/$m_2$ interaction binds the m1 coupled first anti-analyte (now containing analyte) to the label in the labeling zone and this complex (analyte/anti-analyte$_1$/$m_1$/$m_2$/label is picked up by a second anti-analyte, coupled to $m_3$ in a portion of the capture zone, and the entire complex is finally captured by $m_4$ and bound to $m_3$ in the detecting portion of the capture zone as the complex: support/$m_4$/$m_3$/anti-analyte$_2$/analyte/anti-analyte$_1$/$m_1$/$m_2$/label.

Figure 2D:
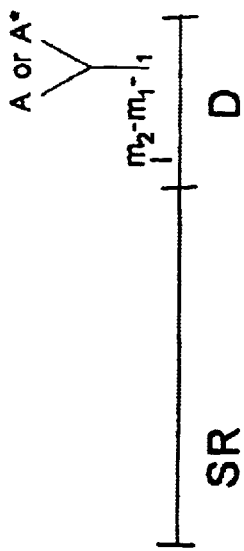
Figure 2D:
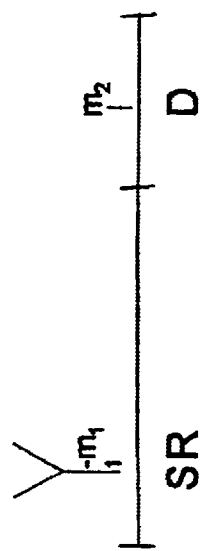

FIG. 2D shows a competitive format wherein a labeled competitor (A*) competes with analyte for binding to anti-analyte/$m_1$. The resulting complexes are carried to the detection zone and captured by $m_1$/$m_2$ binding. The level of labeled competitor in the capture zone is inversely proportional to analyte. The labeled competitor may be supplied in the sample-receiving zone as shown in FIG. 2E or it may be mixed with the analyte prior to supplying the analyte to the sample-receiving zone as shown here. In either case, a labeling zone is unnecessary. The interaction of $m_1$ and $m_2$, in this illustration, assists the capture of the anti-analyte, containing either A or A* in the detecting portion or a test bar in the capture zone.

FIG. 2E shows the alternative form of the assay in FIG. 2D where the A* is supplied in the sample-receiving zone. In this embodiment, where A* already resides in the test strip, the distinction between the sample-receiving zone and the labeling zone is, of course, blurred; the A* could be considered to be present in the sample-receiving zone per se or in a "labeling zone" not necessarily separate from it.

FIG. 2F shows an alternative competitive assay where the competitor for the analyte, designated A' in this figure, is not labeled, but is coupled to $m_1$ in the sample-receiving zone. (A'-$m_1$ could also be mixed with sample prior to application.) When analyte is supplied to the sample-receiving zone, both analyte and A'-$m_1$ travel to the labeling zone where they compete for anti-analyte coupled to label. The analyte coupled to label is lost from the assay, since there is no mechanism for its capture in the detecting portion of the capture zone. On the other hand, the competitor is captured, where the complex is: support/$m_2$/$m_1$/competitor/anti-analyte/label.

Figure 2G:
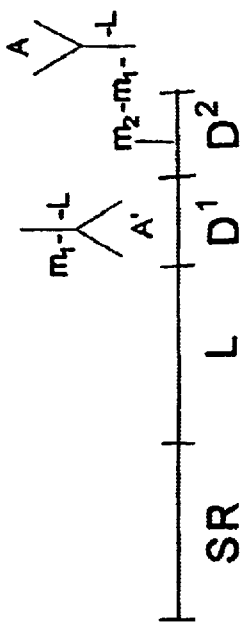
Figure 2G:
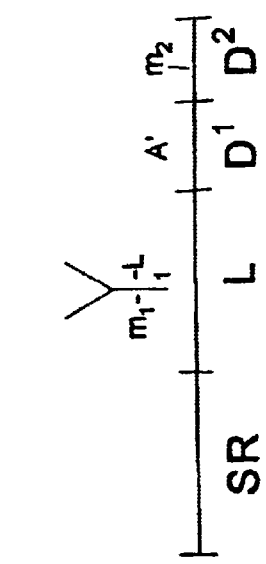
Figure 2H:
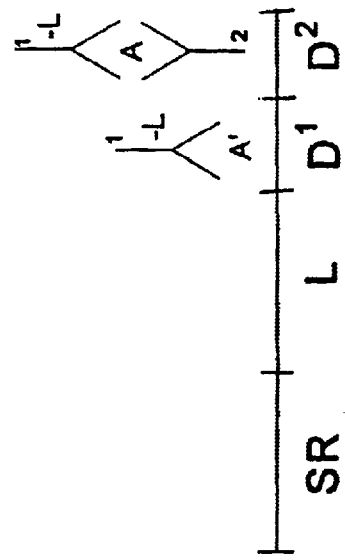
Figure 2H:
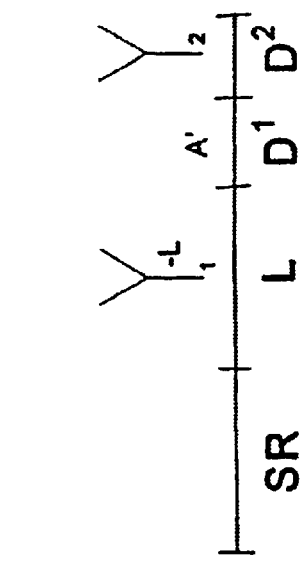

FIGS. 2G and 2H represent embodiments of the invention wherein a competitor to the analyte, unlabeled A', acts as a gatekeeper in a portion of the capture zone which precedes the detecting portion. As shown in FIG. 2G, the labeling zone contains anti-analyte coupled both to label and $m_1$. When analyte is applied to the sample-receiving zone, it flows through the labeling zone picking up anti-analyte coupled to label and to $m_1$. As this complex traverses the gatekeeping portion occupied by A', region $D^1$, A' displaces some of the analyte from anti-analyte. Thus, the A' contained in $D^1$ becomes labeled as shown in a complex which has the form: support/competitor/anti-analyte/(label)/$m_1$. However, that portion of the anti-analyte that is picked up by analyte itself is captured in the detecting portion $D^2$ with a complex of the form: support/$m_2$/$m_1$/anti-analyte/analyte/(label)/.

While the embodiment set forth in FIG. 2G takes advantage of the $m_1$/$m_2$ interaction to assist capture of the labeled analyte in the detecting portion, this mechanism is not necessary in all cases where the capture rate is sufficient. Accordingly, in FIG. 2H, $D^2$ is supplied with a second anti-analyte. In this embodiment, when analyte is applied to the sample-receiving zone, it passes through the labeling zone which contains anti-analyte coupled to label and carries the label through to $D^1$. In $D^1$, A', the competitor, removes some of the anti-analyte coupled label from the analyte itself and captures it in $D^1$. Analyte which remains bound to label is captured in $D^2$ as a sandwich of the form: support/anti-analyte$_2$/analyte/anti-analyte$_1$/label.

It is evident that the formats described in FIGS. 2G and 2H lend themselves to at least semiquantitative determination of analyte, since a comparison can be made between the competitor and the analyte label levels. It is also evident that $D^1$ must be clearly demarked from $D^2$ so that there is no confusion about the origin of the label in either portion of the capture zone.

Another way to make the assay semiquantitative is simply to adjust the concentration of A' so that label will appear in the detecting portion, $D^2$, only when the analyte concentration is above a certain level. The detection level can, of course, be readily adjusted by adjusting the level of A' in the gatekeeping portion, $D^1$.

The following examples are intended to illustrate but not to limit the invention.

EXAMPLE 1

Assay for Human Chorionic Gonadotropin (hCG)

This example illustrates the format shown in FIG. 2A. The sample-receiving zone contains anti-hCG coupled with biotin. The labeling zone contains anti-hCG labeled with a dye complex enzyme conjugate of the type described in WO94/01775. The capture zone contains streptavidin adsorbed to the capture zone through complexion with an appropriate protein. In general, goat γ-globulin, BSA or chicken γ-globulin can be used to aid in the adsorption of streptavidin to the capture zone. The results show that streptavidin used alone in the capture zone is less effective than streptavidin complexed with protein.

The supporting device/test strip used is illustrated in FIG. 1. Table 1 shows the various combinations, described in more detail below, and the observed results. Results are shown with respect to visible label at 10 minutes using hCG as analyte at indicated concentrations (mIU/ml)

TABLE 1

| Test Strip Components | | | Visual Call Assay Results (hCG) at 10 min. | | | |
|---|---|---|---|---|---|---|
| Sample-receiving zone | Labeling Zone | Detection Zone | 0 | 25 | 100 | 400 |
| biotin-goat anti-hCG | monoclonal anti-hCG dye complexed enzyme conjugate | StrAv-goat IgG<br>StrAv-BSA<br>StrAv-chicken IgG | −<br>−<br>− | +<br>+<br>+ | +<br>+<br>+ | NT<br>NT<br>NT |
| biotin-goat anti-hCG (F(ab)₂ | monoclonal anti-hCG dye complexed enzyme conjugate | StrAv-goat IgG<br>StrAv-BSA<br>StrAv-chicken IgG | −<br>−<br>− | +<br>+<br>+ | +<br>+<br>+ | NT<br>NT<br>NT |
| biotin-goat anti-αhCG | monoclonal anti-hCG dye complexed enzyme conjugate | StrAv-goat IgG<br>StrAv-BSA<br>StrAv-chicken IgG | −<br>−<br>− | +<br>+<br>+ | +<br>+<br>+ | NT<br>NT<br>NT |
| biotin-rabbit anti-hCG | monoclonal anti-hCG dye complexed enzyme conjugate | StrAv-goat IgG<br>StrAv-BSA<br>StrAv-chicken IgG | −<br>−<br>− | +<br>+<br>+ | +<br>+<br>+ | NT<br>NT<br>NT |
| biotin-rabbit anti-αhCG | monoclonal anti-hCG dye complexed enzyme conjugate | StrAv-goat IgG<br>StrAv-BSA<br>StrAv-chicken IgG | −<br>−<br>− | +<br>+<br>+ | +<br>+<br>+ | NT<br>NT<br>NT |
| biotin-monoclonal anti-hCG | monoclonal anti-hCG dye complexed enzyme conjugate | StrAv-goat IgG<br>StrAv-BSA<br>StrAv-chicken IgG | −<br>−<br>− | +<br>+<br>+ | +<br>+<br>+ | NT<br>NT<br>NT |
| biotin-monoclonal anti-hCG | StrAv-coated latex beads | rabbit anti-hCG | − | NT | NT | + |
| biotin-rabbit anti-hCG | Monoclonal anti-hCG coated latex beads | StrAv<br>Av | −<br>− | NT<br>NT | NT<br>NT | +<br>+ |

NT = not tested

The following describes in more detail the construction of the assay strip with the various components shown in Table 1.

A. Monoclonal Antibodies

Monoclonal anti-hCG ascites fluid was fractionated at 0–4° by delipidation with sodium dextran sulfate and calcium chloride, followed by ammonium sulfate treatment at 50% salt saturation and desalted on a G25F (Pharmacia Biotech Inc., Piscataway, N.J.) column into 10 mM Tris buffer (pH 8.0) followed by fractionation with Q-Sepharose FF (Pharmacia Biotech, Inc.) resin using a salt gradient of 0 to 0.3M sodium chloride in the same buffer. Fractionation was monitored at 280 nm, and the antibody peak was collected and buffer-exchanged on a G25F column into PBS (Phosphate-Buffer Saline, pH 7.4, Product #7011, Quidel Corporation, San Diego, Calif.). The resultant anti-hCG antibody was diluted in the same buffer to 1 mg/ml.

Monoclonal antibodies against FSH were purified by and purchased from Oy Medix Biochemica AB, Kauniainen, Finland (clones 6602 and 6601).

Polyclonal Antibodies

Polyclonal anti-hCG rabbit serum was mixed with an equal volume of Protein A MAPS II Binding Buffer (Bio-Rad Laboratories, Hercules, Calif.) and applied onto Affi-Prep Protein A (Bio-Rad Laboratories) column equipped with a CF11 guard column. Following washing of unbound materials, the antibodies were eluted with Protein A MAPS II Elution Buffer (Bio-Rad Laboratories) and buffer-exchanged on a G25F column into PBS.

In order to obtain hCG-specific polyclonal antibodies, anti-hCG goat or rabbit serum was fractionated at 0–4° C. by dilapidation with sodium dextran sulfate and calcium chloride followed by ammonium sulfate precipitation at 50% salt saturation and desalted on a G25F column into PBS. To obtain antibodies specific for alpha subunit of hCG, the resultant antibodies were applied onto affinity column containing alpha subunit of hCG covalently attached to ACTI-GEL ALD SUPERFLOW (agarose resin containing monoaldehyde group. (Sterogene Bioseparations, Inc., Arcadia, Calif.) resin. The unbound species were washed with PBS, hCG alpha subunit-specific antibodies were eluted with 0.1 M glycine (pH 2.3) and buffer-exchanged on a G25F column into PBS. To obtain antibodies specific for whole (intact) hCG, the dilapidated and ammonium sulfate fractionated serum (prepared as described above) was applied onto affinity column containing whole (intact) hCG covalently attached to CNBr-activated Sepharose 4B (Pharmacia Biotech, Inc.) resin. The unbound species were washed with PBS, whole hCG-specific antibodies were eluted with 0.1 M glycine (pH 2.3) and buffer-exchanged on a G25F column into PBS.

Fragments

To obtain F(ab')$_2$ fragment of goat antibody specific for whole hCG, the resultant antibody just described was digested with pepsin employing the reagents and procedure advised by UniSyn Technologies, Inc., Tustin, Calif. The resultant F(ab')$_2$ fragments were buffer-exchanged into PBS using a G25F column.

B. Biotin Coupling

Purified antibodies or their fragments, obtained as described in paragraph A at 1 mg/ml in PBS, were biotinylated for 3 hours at 25° C. (ambient temperature) by adding 37 µl of 10 mg/ml solution of NHS-LC-Biotin, Product #21335; Pierce, Rockford, Ill) in anhydrous DMF. Subsequently, the derivatized antibody was buffer-exchanged on a G25F column into PBS and stored at 0–4° C.

C. Preparation of Streptavidin-Carrier Protein Conjugates

To prepare streptavidin-carrier protein conjugates (Scripps Laboratories, San Diego, Calif.; or, ProZyme, Inc., Richmond, Calif.) was dissolved at 6 mg/ml in 0.1 M sodium phosphate buffer (pH 7.0) derivatized by adding N-succinimidyl-3-2-pyridylthio) propionate (Pierce) dissolved at 3 mg/ml in anhydrous ethanol to a final concentration of 25 µg/ml to 1 mg/ml, incubation of the reaction mixture for 45 minutes at 25° C., and buffer exchange on a G25F column into 0.1 M sodium acetate buffer (pH 4.5). Thiol groups on streptavidin were released by adding 1 M dithiotreitol (Sigma Chemical co., St. Louis, Mo.) dissolved in the same buffer to a final concentration of 50 nM, incubation of the reaction mixture for 30 minutes at 25° C., and buffer exchange on a G25F column into 0.1 M sodium phosphate buffer (pH 7.0).

Maleimide groups were introduced into carrier goat IgG (Product #7102; Quidel Corporation), chicken IgY (Jackson Immuno Research Laboratories, Inc., West Grove, Pa.) or BSA (bovine serum albumin, Sigma Chemical co.) at 5 mg/ml in 0.1 M sodium phosphate buffer (pH 7.0) by adding n-maleimidobenzoyl-N-hydroxysuccinimide ester (Pierce) at 8 mg/ml in anhydrous DMF to a final concentration of 400 µg/ml, incubation of the reaction mixture for 45 minutes at 25° C., and buffer exchange on a G25F column into 0.1 M sodium phosphate buffer (pH 7.0). The maleimide-containing carrier proteins and SH-derivatized streptavidin were allowed to react for 2 hours at 25° C. followed by buffer exchange on a G25F column into 50 mM Tris buffer (pH 8.0).

D. Preparation of the Labeling Agents

To prepare antibody-enzyme conjugates, horseradish peroxidase (HRP Biozyme Laboratories International, Ltd., San Diego, Calif.) was prepared at 10 mg/ml in 0.1 M sodium phosphate (pH 8.0) containing 0.5 mM 2-mercaptoethanol, incubated at 25° C. for 45 minutes with 2-inimothiolane (Sigma) at a final concentration of 1.23 mg/ml, before being buffer-exchanged on a G25 column into 0.1 M sodium phosphate (pH 7.3).

The maleimide-containing monoclonal anti-hCG or anti-FSH (clone 6601, specific for the a-subunit) antibody and SH-derivatized enzyme were allowed to react for 2 hours at 25° C. following by separation of the enzyme-antibody conjugate on a Sephacryl® S300 HR resin (Pharmacia Biotech, Inc.). A 0.45 µm filtered conjugate elution buffer composed of 0.05 M sodium phosphate buffer (pH 7.0) containing 0.1% (w/v) NaN$_3$, 0.03% (w/v), MgCl$_2$. 6H$_2$0, 0.003% (w/v) ZnSO$_4$. 7H$_2$O, and 0.4% (w/v) Tween® 20 was used throughout the fractionalization. The fractionalization was monitored at 280 mm, and the antibody-enzyme conjugate fraction pooled. Alternatively, unconjugated HRP was separated from antibody-enzyme conjugate using QAE resin. Subsequently, the antibody-enzyme conjugates were buffer-exchanged on a G25 column into the 0.05 M Tris/HCl buffer (pH 7.5), supplemented with 50 µg gentamicin/ml.

Pre-dyed label complex containing antibody-HRP conjugate was prepared in a 2016 µl incubation reaction at 25° C. by a sequential addition to 360 µl of 0.05 M Tris/HCl buffer (pH 7.5) containing 50 µl of 3 mg of 4 chloro-1-naphthol per ml methanol of the following: (a) 54 µl of 0.05 M Tris/HCl buffer (pH 7.5) containing 50 µgentamicin/ml; (b) 1548 µl of 0.05 M Tris/HCl buffer (pH 7.5) containing 0.22% (v/w) H$_2$O$_2$, 0.1 mM EDTA and 50 µg gentamicin/ml; and finally to initiate the complex formation; (c) 54 µl of 0.27 mg anti-hCG antibody/HRP conjugate in 0.05M Tris/HCl buffer (pH 7.5) containing 50 µg gentamicin/ml. After 15 minutes incubation, the following reagents (chilled to 4° C.) were added: (a) 125 µl of 0.05 M Tris/HCl buffer (pH 7.5) containing 50 µg gentamicin/ml; (b) 126 µl of 0.5 M Tris/HCl buffer (pH 7.5) containing 0.02% (v/v) H$_2$O$_2$, 0,1 mM EDTA and 50 µg gentamicin/ml; and (c) 252 µl of 100 mg mBSA in 0.05 Tris/HCl buffer (pH 8.0).

The mixture was poured onto Sontara spunlace fabric at 38 µl/cm$^2$. The matrix was kept at room temperature for 20 minutes and abruptly frozen at −70° C., along with the lyophilization flask for at least an hour. The resulting composition was lyophilization overnight on Virtis lyophilizer and the intermediate pre-dyed labeling pads were cut into 10×3 mm rectangles with the spunlace fibers parallel to the longer side of the paid.

Colored Latex Labeling A gent

"Test" beads for labeling analyte, containing monoclonal anti-hCG, were prepared as follows:

One-half (0.5) ml of 0.45µ red latex beads (Bang Laboratories, Inc., Carmel, Ind.) were washed twice with 1 ml of 50 mM Tris buffer (pH 8.0) by sonicating for 10 minutes and recovered by microcentrifugation for 3 minutes. To the pelleted beads was added 05 ml of coupling solution, in this case consisting of 0.8 mg/ml monoclonal anti-hCG and 0.2 mg/ml methylated BSA in the same buffer. The pellet was resuspended and sonicated for 10 minutes, and then rotated overnight at room temperature. After centrifugation for 3 minutes, the supernatant was aspirated and the bead pellet was resuspended in 05 ml of the 10 mg/ml methylated BSA and rotated end-over-end for 4 hours at room temperature. After centrifugation and removal of the supernatant, the pellet is washed three times with bead storage solution as described above, and the final bead preparation was at a concentration of 1% solids.

"Test" beads for labeling analyte with streptavidin or avidin (Scripps Laboratories) were prepared in the same manner.

Finally, to prepare the labeling zone, the test beads were diluted into methylated BSA at a concentration of 0.05% solids. The resultant mixture was stirred and poured onto a Sontara 0-100 DuPont spunlace fabric membrane at 47.6 µl/cm$_2$. The labeled pad was then kept at room temperature for 5 minutes and frozen at −70° C., along with the lyophilizing flask for at least an hour. The resulting membranes were lyophilized overnight on Virtis lyophilizer. The label-containing pads were then cut into 10×7.5 mm rectangles with the spunlace fibers parallel to the longer side of the pad.

Assay

The test strips were assembled as shown in FIG. 1 and the sample to be tested applied to the sample-receiving zone.

After ten minutes, the presence or absence of analyte was detected visually on the test bar in the capture zone. The results are shown in Table 1 above for various combinations of label and capture reagents.

EXAMPLE 2

Assay for FSH

Using an approach similar to that set forth in Example 1, FSH was measured at various concentrations visually using Gretag Density Units (GDU) and compared to a reference strip in the capture zone containing goat anti-mouse IgG (Quidel Product #7362) at 0.5–1.0 mg/ml PBS, which captures the HRP/monoclonal conjugate contained in the labeling pad. The sample, containing 0–60 mIU/ml of FSH is applied to the sample pad made of New Merge Sontara which was treated with 39 $\mu$l/cm$^2$ of 10 mg/ml methylated-BSA and then with biotinylated monoclonal anti $\beta$-FSH subunits (clone 6602) and spotted at 80 ng/cm$^2$ in PBS followed by lyophilization.

The sample flows through a label pad which contains lyophilized predyed label complex containing antibody (clone 6601, specific for the $\alpha$-FSH subunit) coupled to HRP. The capture zone, which is nitrocellulose, contains a test line of streptavidin-IgG spotted at 0.25 mg/ml in PBS, and a reference line of goat anti-mouse IgG at 0.4 mg/ml in PBS. The capture zone is then blocked with 10 mg/ml methylated BSA containing trehalose. The strip is supplied with a standard absorbent for an assay time of 10 minutes.

The results are plotted in GDU as a function of FSH concentration as shown in FIG. 3. As analyte concentration increases, signal intensity of the test line increases and the resulting signal intensity of the reference line decreases. Signal crossover occurs at the cut-off level of 40 mIU.

What is claimed is:

1. A test strip suitable for a lateral flow assay, which test strip comprises a sample-receiving zone, a labeling zone and a capture zone, wherein said sample-receiving zone contains a single movably bound first anti-analyte coupled to a first member of a first specific binding pair irrelevant to analyte/anti-analyte interaction, wherein said labeling zone contains a movably bound counter member of said first specific binding pair irrelevant to analyte/anti-analyte interaction, said counter member is coupled to a label, and wherein said capture zone is separated into a gatekeeping zone proximal to said sample-receiving zone that contains a movably bound second anti-analyte coupled to a first member of a second specific binding pair irrelevant to analyte/anti-analyte interaction and a detecting zone distal to said sample-receiving zone that contains an immobilized counter member of said second specific binding pair irrelevant to analyte/anti-analyte interaction.

2. The test strip of claim 1, wherein the first and second anti-analyte is an antibody or an immunologically reactive portion thereof immunospecific for the analyte.

3. The test strip of claim 1, wherein the specific binding pair is avidin or streptavidin and biotin.

4. A method to determine the presence, absence or amount of an analyte in a sample in a one-step lateral flow assay conducted on a test strip, which method comprises:

a) providing a test strip suitable for a one-step lateral flow assay, which test strip comprises a sample-receiving zone, a labeling zone and a capture zone, wherein said sample-receiving zone contains a single movably bound first anti-analyte coupled to a first member of a first specific binding pair irrelevant to analyte/anti-analyte interaction, said labeling zone contains a movably bound counter member of said first specific binding pair irrelevant to analyte/anti-analyte interaction, said counter member is coupled to a label, and said capture zone is separated into a gatekeeping zone proximal to said sample-receiving zone that contains a movably bound second anti-analyte coupled to a first member of a second specific binding pair irrelevant to analyte/anti-analyte interaction and a detecting zone distal to said sample-receiving zone that contains an immobilized counter member of said second specific binding pair irrelevant to analyte/anti-analyte interaction;

b) applying a fluid sample containing or suspected of containing an analyte to said sample-receiving zone, and allowing said sample to flow through said labeling zone and into said capture zone and carrying said analyte, if present, said first anti-analyte, said movably bound counter member and said movably bound second anti-analyte into said detecting zone to form a first anti-analyte/analyte/second anti-analyte complex, wherein said label is linked to said complex through the interaction between said first member and counter member of said first specific binding pair and said second anti-analyte in said complex is bound to said test strip through the interaction between said first member and counter member of said second specific binding pair; and c) assessing the presence, absence or amount of label in said first anti-analyte/analyte/second anti-analyte complex to determine the presence, absence or amount of said analyte in said sample.

5. The method of claim 4, wherein the first and second anti-analyte is an antibody or an immunologically reactive portion thereof immunospecific for the analyte.

6. The method of claim 4, wherein the specific binding pair is avidin or streptavidin and biotin.

* * * * *